(12) United States Patent
Lathem

(10) Patent No.: US 8,297,435 B2
(45) Date of Patent: Oct. 30, 2012

(54) METHODS AND APPARATUS FOR GERMICIDAL IRRADIATION OF CHECKOUT SYSTEM SURFACES

(75) Inventor: Jonathan Lathem, Jefferson, GA (US)

(73) Assignee: NCR Corporation, Duluth, GA (US)

( * ) Notice: Subject to any disclaimer, the term of this patent is extended or adjusted under 35 U.S.C. 154(b) by 218 days.

(21) Appl. No.: 12/820,272

(22) Filed: Jun. 22, 2010

(65) Prior Publication Data

US 2011/0308917 A1    Dec. 22, 2011

(51) Int. Cl.
*G01N 23/00*    (2006.01)

(52) U.S. Cl. ...... 198/617; 198/494; 422/24; 250/455.11

(58) Field of Classification Search ............... 198/493, 198/494, 571, 577; 422/24; 250/454.11, 250/455.12
See application file for complete search history.

(56) References Cited

U.S. PATENT DOCUMENTS

| | | | |
|---|---|---|---|
| 4,309,388 A * | 1/1982 | Tenney et al. | 422/304 |
| 4,877,964 A * | 10/1989 | Tanaka et al. | 250/455.11 |
| 5,114,670 A * | 5/1992 | Duffey | 422/24 |
| 5,326,542 A * | 7/1994 | Sizer et al. | 422/291 |
| 5,958,336 A * | 9/1999 | Duarte | 422/24 |
| 6,851,545 B1 * | 2/2005 | Carter | 198/494 |
| 6,971,503 B2 | 12/2005 | Thompson | |
| 7,160,566 B2 * | 1/2007 | Fink et al. | 426/235 |
| 7,225,115 B2 | 5/2007 | Kelly et al. | |
| 7,234,586 B1 * | 6/2007 | Newman | 198/495 |
| 7,791,044 B1 * | 9/2010 | Taylor et al. | 250/455.11 |

OTHER PUBLICATIONS

"Ultraviolet germicidal irradiation", http://en.wikipedia.org/wiki/Ultraviolet_germicidal_irradiation.

* cited by examiner

*Primary Examiner* — Douglas Hess
(74) *Attorney, Agent, or Firm* — Peter Priest

(57) ABSTRACT

A germicidal irradiation approach to killing germs on conveyors and other check out surfaces in stores, such as grocery stores, which sell articles such as food items where possible contamination from leaks and the like is a concern. An adaptable, portable ultraviolet light apparatus is provided to irradiate surfaces such as conveyor belts.

10 Claims, 6 Drawing Sheets

METHODS AND APPARATUS FOR GERMICIDAL IRRADIATION OF CHECKOUT SYSTEM SURFACES

FIELD OF THE INVENTION

The present invention relates generally to advantageous methods and apparatus for killing germs on checkout system surfaces, and more particularly to arrangements for employing an ultraviolet (UV) light apparatus to irradiate surfaces such as checkout conveyor belts.

BACKGROUND OF THE INVENTION

When shopping for groceries or other items, who has not encountered a situation where one is asked to place an item on a checkout conveyor belt or other checkout system surface where you are not sure about what has been recently placed on that surface? Or, alternatively, one may be exposed to a particular situation where one has observed someone place a leaking item like a poultry product where the leak has smeared the surface and caused concerns about salmonella or other germs contaminating items later placed on the conveyor.

While checkout clerks are trained to actively to respond to such spills with products such as Windex™ and paper towels, even a small amount of unaddressed contamination may leave questions in a consumer's mind. Further, as self-checkout increases and demands on the time of checkout clerks increase, less time and opportunities may exist for appropriate prophylactic action to be taken.

Perhaps, as a consequence, various complex conveyor belt cleaning apparatuses have been described. See, for example, U.S. Pat. Nos. 7,225,915 and 6,971,503 which are incorporated by reference herein in their entirety. However, such arrangements are relatively complex, and if built into the conveyor and not seen by consumers may fail to ease the consumer's fears about germs and the like. Also, if built into a conveyor belt system, such an approach does not provide for ready retrofitting to an existing store system, nor would it have the flexibility of being moved from one checkout station to another as needed.

SUMMARY OF THE INVENTION

Among its several aspects, the present invention addresses an ultraviolet light arrangement to provide germicidal irradiation which may be readily adapted to a wide array of existing and future checkout systems.

Among its several aspects, the present invention addresses approaches which stores can easily retrofit to their current conveyor belt and other systems. The UV germicidal irradiation approach involves fewer moving parts than an active belt cleaning system so that a reduced number of parts are employed which can break or wear out. The UV light approach also involves less ongoing maintenance as there is no water or cleaning fluid to replace or refill. Also, the UV light system is readily visible to the customer so the customer will see it and know it is working thereby addressing concerns about germs and the like. Additionally, this approach may be cheaper as there are not any fans, pumps, or the like involved.

A more complete understanding of the present invention, as well as further features and advantages of the invention, will be apparent from the following Detailed Description and the accompanying drawings.

DETAILED DESCRIPTION

Figure 1:
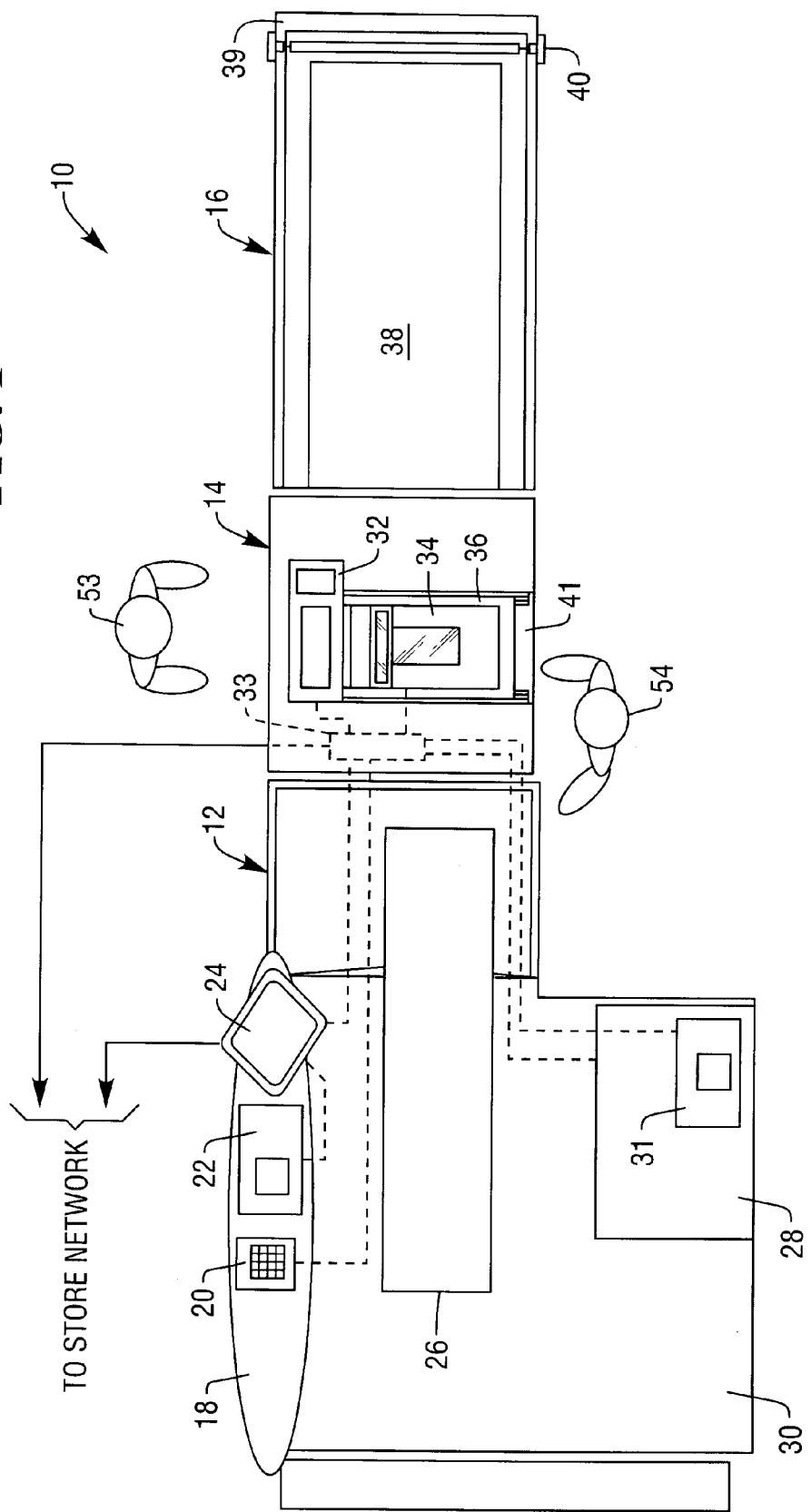
FIG. 1 is a top view of a checkout system modified in accordance with the present invention to employ an ultraviolet light apparatus in accordance with the present invention.

Referring now to FIG. 1, system 10 is configured as a full-service checkout island and includes bagging portion 12, scanning portion 14, and receiving portion 16.

Bagging portion 12 includes customer service table 18, conveyor 26, cash drawer 28, bagging shelf 30, and receipt printer 31.

Customer service table 18 provides a convenient writing surface and includes card reader with pin keypad 20, customer receipt printer 22, and customer display 24.

Card reader 20 is operational in both full and self-service configurations.

Printer 22, though present in the full-service configuration, is intended primarily for operation as a receipt printer during the self-service mode of operation. Printer 31 is used for full-service operation.

Customer display 24 operates as a customer information terminal during full-service operation and a customer-operated transaction terminal during self-service operation. Customer display 24 is preferably connected to a store network. An NCR 7401 computer terminal is suitable for use as customer display 24.

Conveyor 26 supports and transports merchandise items to bagging shelf 30. Conveyor 26 preferably telescopes to allow a portion of bagging portion 12 to be lowered to become a bagging shelf in the self-service mode of operation.

Cash drawer 28 is operated by a full-service checkout employee and allows the employee to process cash and check payments and dispense change.

Scanning portion 14 includes terminal interface 32, dual-aperture bar code scanner 34, and terminal 33.

Terminal interface 32 provides an operator with control during a full-service checkout operation. Terminal interface 32 includes either a display and keypad or a touch screen and is mounted above the vertical aperture portion of dual-aperture bar code scanner 34. An NCR Dynakey® terminal is suitable for use as terminal interface 32 although it will be recognized other terminals may also suitably be employed.

Dual-aperture bar code scanner 34 includes vertical aperture and horizontal aperture. Horizontal aperture is substantially flush with the top surface of scanning portion 14 and may be part of a scale weigh plate if dual-aperture bar code scanner 34 is equipped with a scale. An NCR 7875 scanner is suitable for use as scanner 34.

The vertical aperture and its associated scanner housing portion are above the top surface of scanning portion 14. The vertical aperture faces an operator during scanning. Thus, in the full-service configuration of FIG. 1, full-service checkout employee 54 can easily scan merchandise items using scanning light beams from both vertical and horizontal apertures.

Terminal 33 is located within scanning portion 14. Terminal 33 is preferably connected to a store network. During full-service operation, terminal 33 controls card reader 20, cash drawer 28, receipt printer 31, terminal interface 32, and dual-aperture scanner 34.

Figure 3:
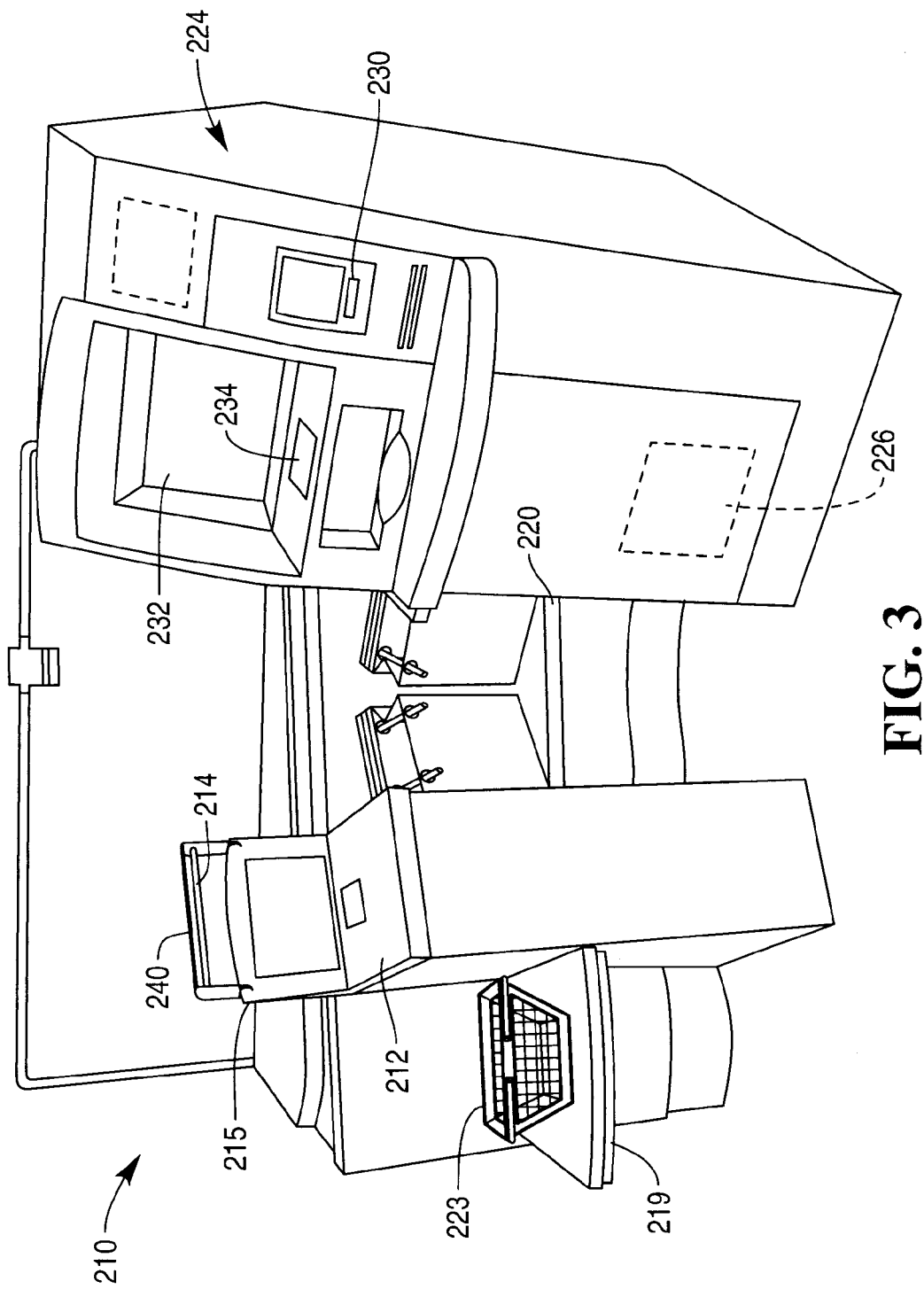
FIG. 3 is a perspective view of a further checkout system modified in accordance with the present invention to employ an ultraviolet light apparatus in accordance with the present invention.

Receiving portion 16 includes conveyor belt 38. An ultraviolet light apparatus 40 in accordance with the present invention is attached to front end of 39 system 10 prior to the beginning of conveyor belt 38. Further details of this ultraviolet light apparatus 40 are shown in FIG. 3 and described below.

During full-service operation, customer 53 approaches receiving portion 16 and places merchandise items on conveyor belt 38. As the conveyor belt 38 moves it is irradiated with ultraviolet germicidal irradiation by ultraviolet light apparatus 40.

Employee 54 scans barcoded merchandise items using dual-aperture bar code scanner 34. Employee 54 may alternatively process bar coded merchandise items by entering price look-up numbers into terminal interface 32. Employee 54 also processes non-barcoded items, such as produce items using the scale of dual-aperture bar code scanner 34 and terminal interface 32. Employee 54 moves all merchandise items to bagging portion 12.

Customer 53 moves to customer service table 18 to wait for all items to be processed by employee 54 and to complete payment. While waiting, customer 53 may view promotional material displayed by display 24 or use customer display to find information about products, answer surveys, or select coupons. Payment may be recorded by card reader 20.

Following payment, employee 54 hands a receipt from receipt printer 31 to customer 53. Customer 53 then removes the items from bagging portion 12.

Further details of the system 10 are found in U.S. Pat. No. 6,286,758 which is assigned to the assignee of the present application and incorporated by reference herein in its entirety. In the system shown and described in U.S. Pat. No. 6,286,758, the scanner 34 can be rotated to face the customer as further described therein for use in a self-checkout mode of operation. It will be appreciated that an ultraviolet lighting arrangement in accordance with the present invention can be employed in a wide variety of checkout and self-checkout contexts.

Figure 2:
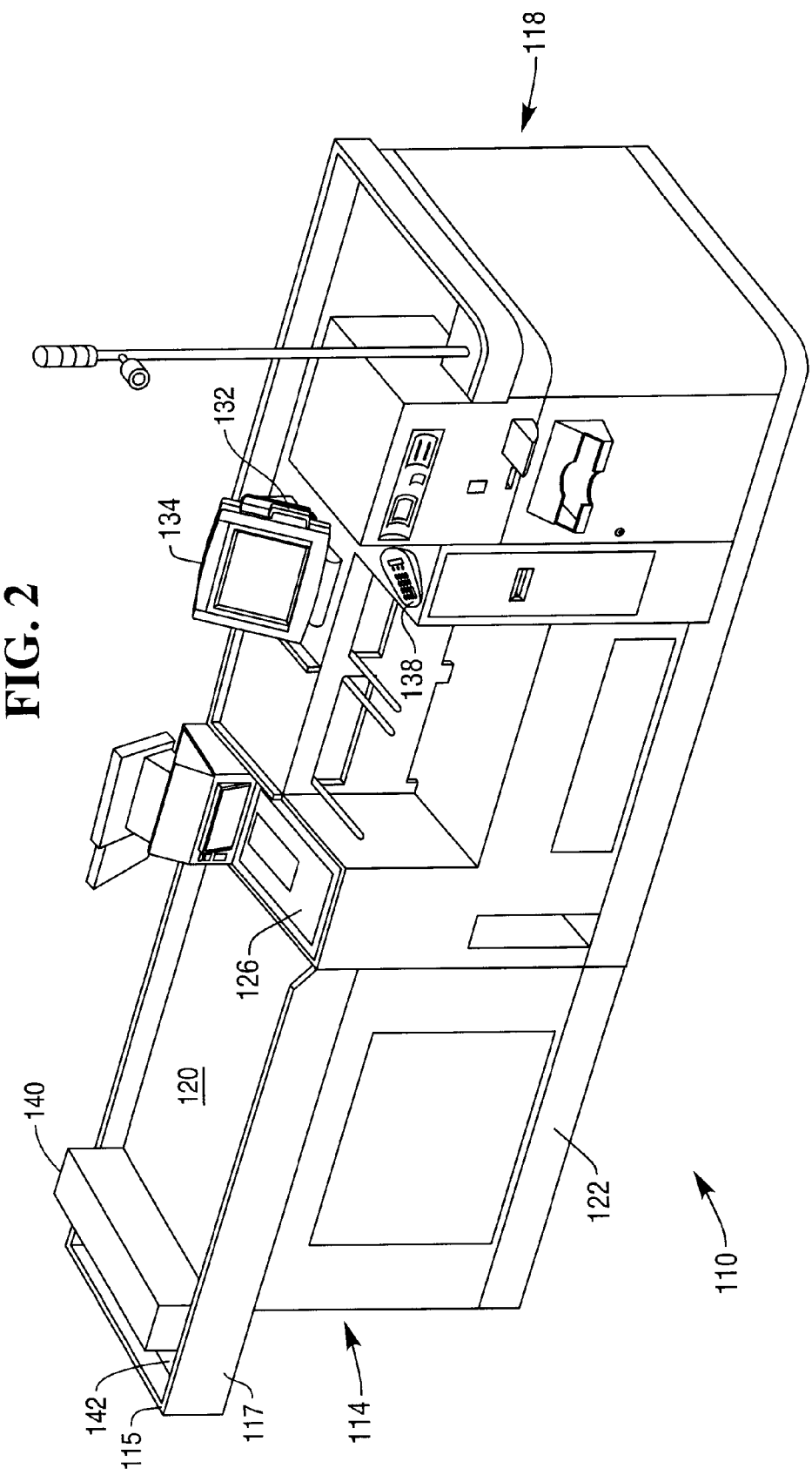
FIG. 2 is a perspective view of a further checkout system modified in accordance with the present invention to employ an ultraviolet light apparatus in accordance with the present invention.

As examples, FIGS. 2 and 3 illustrate further checkout systems 110 and 210, respectively, employing UV light apparatus 140 and 240, respectively, in accordance with the present invention. Checkout station 110 may suitably include a feeder unit 114 and a checkstand 118. Feeder unit 114 includes a feeder belt 120 and housing 122 for the motor and control circuitry that operates feeder belt 120. Feeder unit 114 is movably coupled to checkstand 118 so the feeder belt may be aligned with scanner/scale unit 126. Checkstand 118 includes scanner/scale unit 126, consumer terminal 134, a payment terminal 138 for entry of payment data, and receipt printer 144. Scanner/scale unit 126 uses a laser shining on a glass or other transparent platen to input data from bar codes applied to products or packages. Unit 126 may also include a scale for measuring the weight of articles that are sold on a price/unit of weight basis. Consumer terminal 134 displays article data as it is entered through scanner/scale unit 126. Payment terminal 138 may be any known POS terminal that incorporates a card reader 132 to support credit card, debit card, and other payment methods. A receipt printer provides a consumer with a receipt itemizing the articles purchased and the method of payment. Further details of check stand 110 are found in U.S. Pat. No. 7,673,796 assigned to the assignee of the present invention and incorporated by reference herein in its entirety.

As seen in FIG. 2, the system 110 further includes a UV light apparatus 140 described in further detail in connection with FIG. 5 below. The UV light apparatus 140 shines ultraviolet germicidal irradiation on feeder belt 120.

FIG. 3 shows a self-checkout terminal 210 used in a supermarket setting. The terminal 210 includes a product weight scale 212 and a scanner 214 associated with the scale. A bagging scale 220 is provided adjacent the scanner to support grocery bags into which the customer places each newly scanned item. The terminal 210 includes a basket scale 219 configured to support a shopping basket 223 full of products. Each of the scales 212, 219 and 220 include at least one weight detector, such as a pressure sensor or a load cell sensor, which is operable to generate a signal in response to the weight of the item placed on the scale. A kiosk 224 includes a display 232, data input device 234 and a payment device 230. A computer or processor 226 is resident within the terminal and executes various software routines associated with the self-checkout process.

An ultraviolet light apparatus 240 clips onto a top edge 215 of scanner 214 to illuminate the top surface bagging scale 220 with UV germicidal irradiation as discussed further below.

Figure 4:
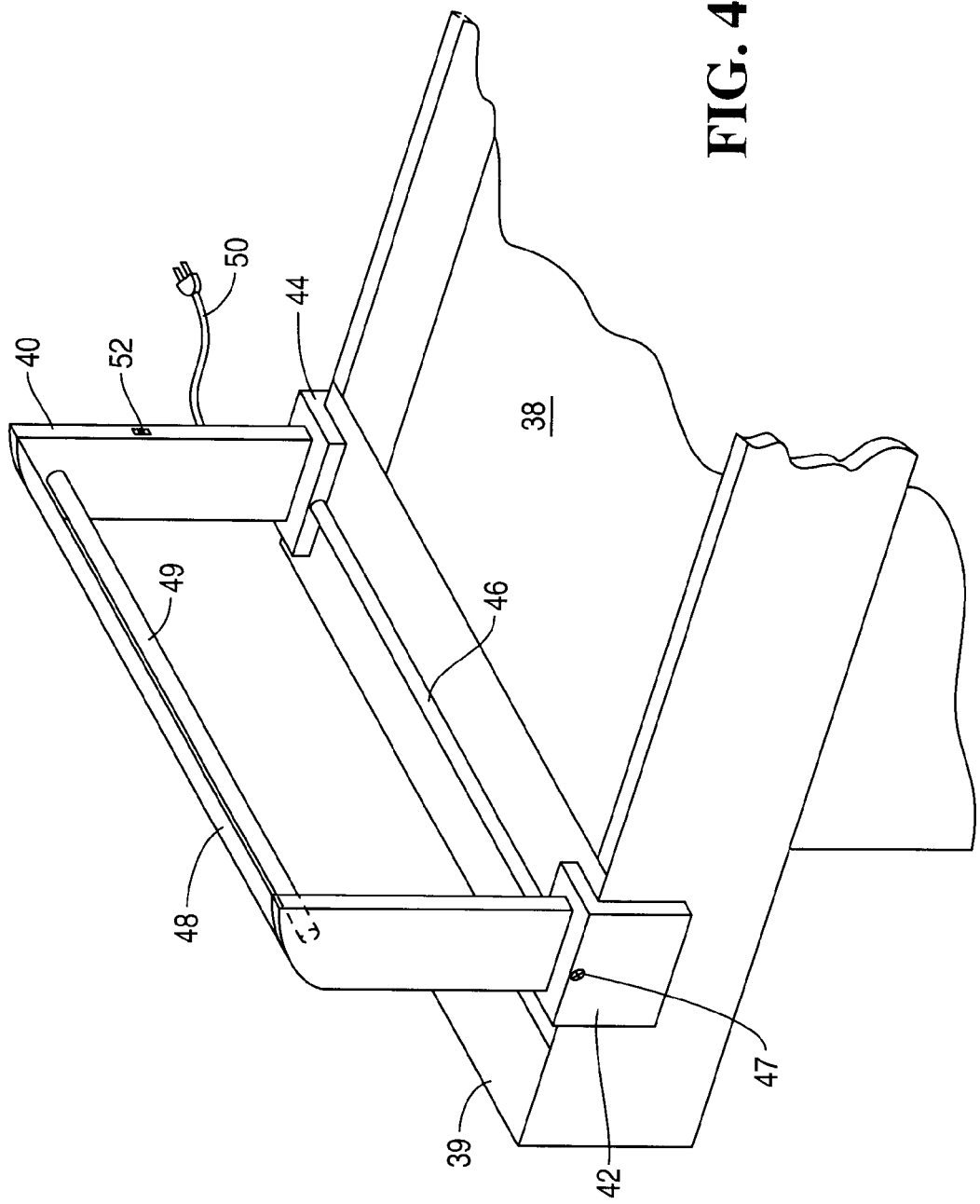
FIG. 4 is a perspective view of an ultraviolet light suitable for user in FIG. 1.

FIG. 4 shows a perspective cutaway view of an exemplary UV light apparatus 40 attached to lead end 39 of the system 10 to illuminate conveyor belt 38 with UV germicidal irradiation as it cycles beneath. As seen in FIG. 4, UV light apparatus 40 comprises two L-shaped clamping brackets 42 and 44, a stiffening and tightening rod 46 having a keyed end 47 for adjustment, a reflective hood arrangement 48, and a UV bulb or source 49, such as a mercury lamp. To prevent incidental exposure to store workers and customers, the height of light 40 will preferably be shallow and hood 48 will be angled to shield observer's eyes and to direct germicidal irradiation downward to the belt 38. In FIG. 4, the height has been exaggerated for ease of illustration and the hood has not been extended and angled so that lamp 49 can be illustrated. It will be recognized a taller unit can be utilized where the unit is to be used solely after hours or other times when customers and store workers are not in the store.

To install the UV light apparatus 40, an operator utilizes a tool matching the keyed end 47 to loosen the rod 46. In a simple embodiment, a Philips head screw driver may match a Philips keyed end 47. A threaded end of rod 46 fitting a threaded opening in L-shaped clamp 44 is turned by turning the keyed end 47 thereby spreading clamps 42 and 44 apart slightly with each turn. If vandalism or meddling is a problem, a special tool and more complex matching key-shaped end 47 may be employed to complicate or eliminate such problems.

With clamps 42 and 44 slightly spread to facilitate installation, the clamps 42 and 44 are slipped down over the lead end 39 of a checkout station such as system 10. Then, the tightening rod 46 is tightened to clamp the UV light 40 in place. It will be noted that such an arrangement has the advantage of allowing a store to move a UV light apparatus 40 to wherever in the store it is needed.

In one embodiment where a power outlet is readily available, a plug 50 is employed to provide power for UV light apparatus 40, and an on and off switch 52 may be utilized to turn the UV light apparatus 40 on and off. Where power is not readily available, a rechargeable battery and charging circuitry may be included in the body of hood arrangement 48. In this arrangement, plug 50 may be detachable and used where and when power is available or to recharge the UV light apparatus during periods of non-use or when recharging is necessary.

Figure 5:
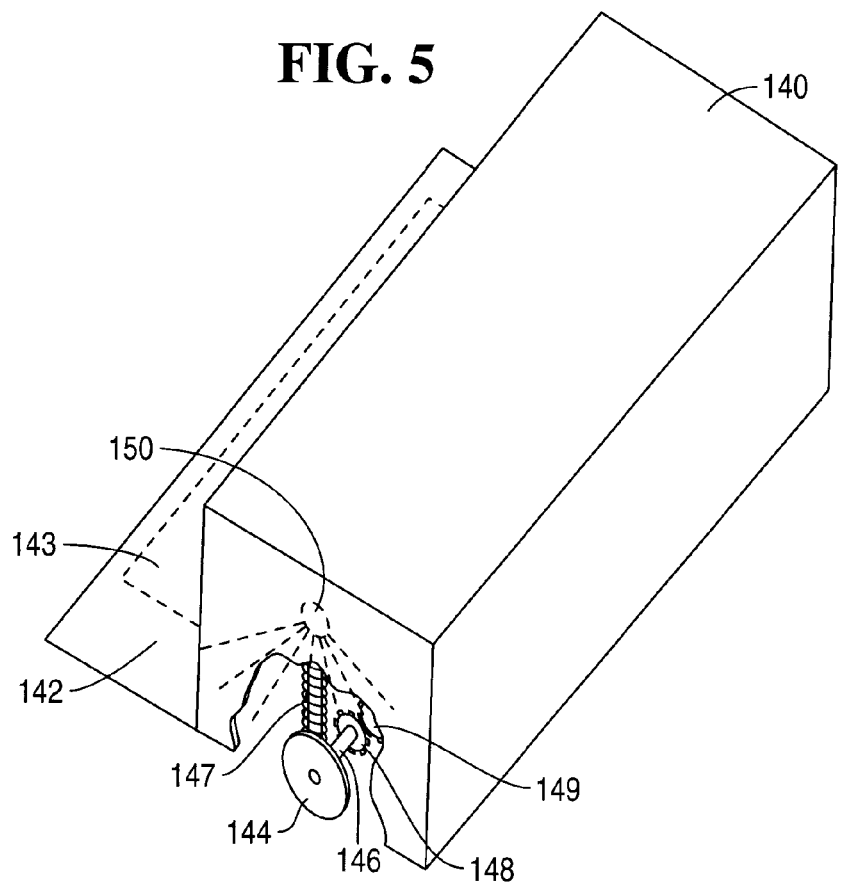
FIG. 5 is a perspective view of an ultraviolet light apparatus suitable for use in FIG. 2.

FIG. 5 shows an alternative embodiment of a UV light apparatus according to the present invention suitable for use as the UV light apparatus 140 of FIG. 2. In this arrangement, at least part of the power for operation is derived from the belt 120. As seen in FIG. 5, a wheel 144 on a shaft 146 is spring biased by a spring 147 against the belt 120. As belt 120 moves, wheel 144 turns rotating shaft 146. A gear or other mechanism, such as gears 148 and 149 can be utilized to drive a generator (not shown) which is utilized to charge a battery to power the UV light apparatus 140. To conserve power, a detector mechanism may be suitably employed to detect rotation of the shaft 146 or movement of belt 120 as discussed further below in connection with FIG. 7. Upon detection of such movement, the UV light apparatus 140 is then turned on. Such an arrangement or a variation thereof allows the flexibility to operate for extended periods without external power as the power derived from movement of the belt 120 supplements or recharges the battery of the UV light apparatus 140.

Additionally in FIG. 5, a suction clamping or magnetic attachment mechanism 143, if appropriate, in portion 142 attaches to top surface 115 of lead end 117 of checkout system 110.

It will be noted that the enclosure of UV light apparatus 140 may be made of lightweight aluminum with a reflective interior so that UV germicidal irradiation from bulb 150 shown in dashed lines if effectively directed downwards to the belt as bulb 150 is substantially completely enclosed by the reflective enclosure. This enclosure reduces the chance of inadvertent harmful exposure to the UV germicidal irradiation.

Figure 6:
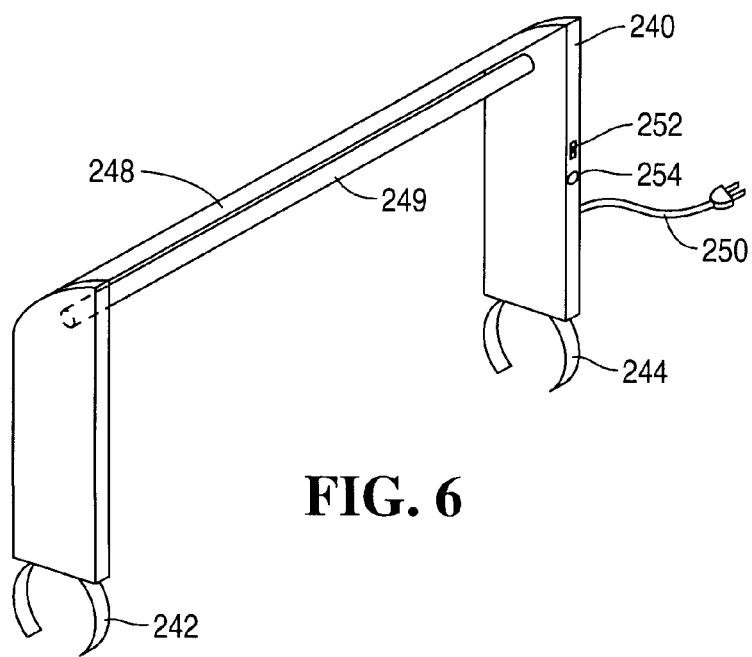
FIG. 6 is a perspective view of an ultraviolet light apparatus suitable for use in FIG. 3.

FIG. 6 shows an alternative embodiment of a UV light apparatus according to the present invention suitable for use as the UV light apparatus 240 of FIG. 3. The UV light apparatus 240 has pairs of clips 242 and 244 which clip onto top edge 215 of scanner scale 212. Hood 248 reflects UV germicidal irradiation down from bulb or source 249 to the top surface of the scanner scale 212. To avoid exposure, the apparatus 240 would be clipped on prior to store closing, plugged in using plug 250, turned on using switch 252, and an internal timer would then turn bulb 249 after a predetermined time. An infrared sensor 254 to detect body heat could be optionally included to detect human presence by sensing body heat nearby and a control system responsive thereto would turn off the apparatus 240.

While the embodiments described up to now have been relatively simple for reasons of cost effectiveness, ease of retrofitability, and the like, it will be recognized that a wide variety of more complex control arrangements may be employed where it is possible to wire control circuitry of a UV light apparatus, such as, UV light apparatus 140, for example, into the belt motor control circuitry for controlling movement of a belt, such as belt 120.

Figure 7:
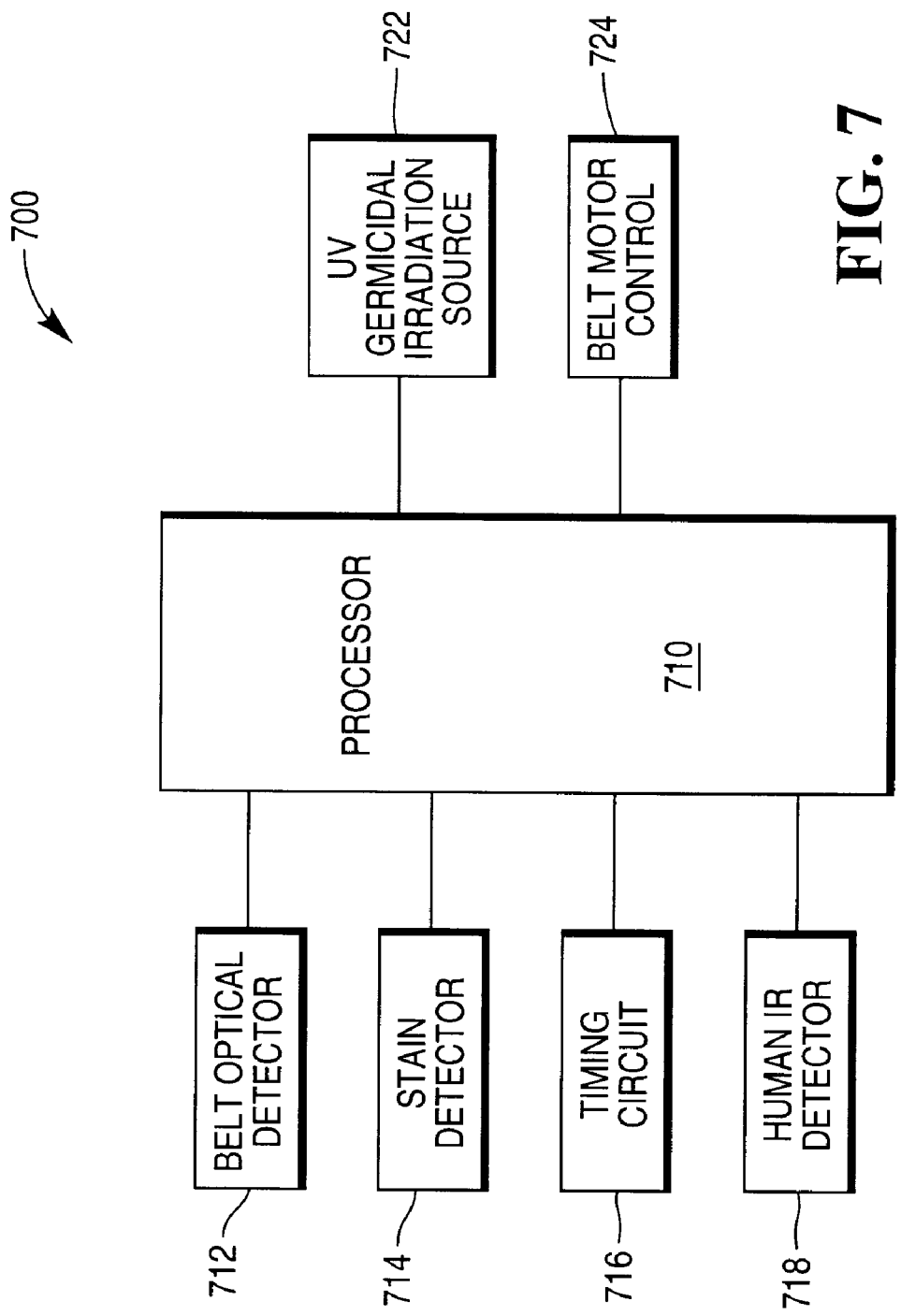
FIG. 7 is a block diagram of a control system for integrating the monitoring of belt motion and selective germicidal irradiation thereof in accordance with the present invention.

In such a circumstance, it may be advantageous to use a programmed microprocessor control system 700, such as the one illustrated in FIG. 7. In the control system 700, processor 710 receives a plurality of inputs including the output of an optical detector 712 which detects motion of the belt 120, a stain detector 714 which optically scans the belt 120 and produces an output indicating a stain has been detected, a timing circuit 716 and an infrared (IR) sensor 718 for sensing human presence within a predetermined distance of the apparatus 140. While these exemplary inputs 712, 714, 716 and 718 are shown, it will be recognized that others may replace them or be added thereto.

Processor 710 is further illustrated as producing outputs which drive a UV germicidal irradiation source 722, such as lamp or bulb 150, and control belt motor control circuitry 724. In one exemplary operation, after store hours, UV light apparatus 140 is to be employed to irradiate the entire belt 120 for a predetermined time, such as ten minutes. Assuming the footprint of the base of apparatus 140 is one foot by the width of the belt, a first one foot portion of belt 120 is irradiated for ten minutes. The belt 120 is then advanced one foot and irradiated and the process is continued until completed. In an alternative approach, the belt 120 may be advanced under stain detector 714. As stains are detected, the belt 120 is stopped and irradiated so that particular attention is applied to questionable areas. A record of stains recently treated could be stored in memory so that a control processor determination could be made not to retreat the same spot over and over.

While the present invention has been disclosed in the context of various aspects of presently preferred embodiments, it will be recognized that the invention may be suitably applied to other environments consistent with the claims which follow.

I claim:

1. A portable ultraviolet (UV) germicidal irradiation method comprising:
   mounting a portable germicidal irradiation system to a checkout surface to be irradiated utilizing a releasable attachment mechanism;
   irradiating the checkout surface with a source of UV germicidal irradiation;
   supporting and shielding the source with a housing;
   utilizing a conveyor belt motion control detector to detect conveyor belt motion; and
   controlling the timing of turning on and off the source by a processor whereby the source is turned on when conveyor belt motion is detected and the source is turned off when conveyor belt motion is not detected.

2. The portable UV germicidal irradiation method of claim 1 wherein the checkout surface to be irradiated comprises a checkout system conveyor belt and the attachment mechanism is adapted for ready attachment to and detachment from a front portion of the checkout system proximate where the checkout system conveyor belt begins.

3. The portable UV germicidal irradiation method of claim 2 further comprising:
   completely surrounding the source on three sides with the housing; and
   arranging the source to direct irradiation downwardly, wherein when the system is mounted proximate the checkout system conveyor belt, the checkout system conveyor belt substantially completes enclosure of the source on a fourth side.

4. The portable UV germicidal irradiation method of claim 1 wherein the surface to be irradiated further comprises a surface of a checkout station other than the checkout system conveyor belt exposed to contact with grocery items and customers' hands.

5. The portable UV germicidal irradiation method of claim 1 wherein the step of mounting further comprises utilizing an adjustable clamping mechanism.

6. The portable UV germicidal irradiation method of claim 1 further comprising deriving power utilized to power the source of UV germicidal irradiation from movement of the conveyor belt utilizing a mechanical arrangement.

7. The portable UV germicidal irradiation method of claim 6 further comprising charging a rechargeable battery by the mechanical arrangement.

8. The portable UV germicidal irradiation method of claim 1 further comprising sensing a person proximate said system utilizing a sensor; and controlling automatically switching the source of UV germicidal irradiation off utilizing the processor when a person is detected proximate the system.

9. The portable UV germicidal irradiation method of claim 1 further comprising utilizing the processor to control the source of UV germicidal irradiation so that a section of the checkout system conveyor belt is exposed thereto for a predetermined time.

10. The portable UV germicidal irradiation method of claim 9 further comprising:
controlling movement of the checkout system conveyor belt utilizing the processor.

* * * * *